(12) United States Patent
Mizutani et al.

(10) Patent No.: US 6,182,498 B1
(45) Date of Patent: Feb. 6, 2001

(54) OXYGEN SENSOR

(75) Inventors: Akio Mizutani, Nagoya; Teppei Okawa, Kounan; Hiroshi Kubota, Wako; Seiichi Hosogai, Wako; Hiroyuki Fujita, Wako, all of (JP)

(73) Assignee: NGK Spark Plug Co., Ltd., Tokyo (JP)

( * ) Notice: Under 35 U.S.C. 154(b), the term of this patent shall be extended for 0 days.

(21) Appl. No.: 09/236,336

(22) Filed: Jan. 25, 1999

(30) Foreign Application Priority Data

Jan. 28, 1998 (JP) .................................................. 10-016029

(51) Int. Cl.$^7$ .......................... G01N 19/10; G01N 27/26; F01N 3/00; F02D 41/00
(52) U.S. Cl. ........................... 73/23.32; 60/274; 123/691; 204/425
(58) Field of Search ............................... 73/23.31, 23.32; 60/274, 276; 123/691; 204/425, 426, 429

(56) References Cited

U.S. PATENT DOCUMENTS

| | | | |
|---|---|---|---|
| 4,683,049 | 7/1987 | Nakajima et al. | 204/428 |
| 5,443,711 | 8/1995 | Kojima et al. | 204/429 |
| 5,707,504 | 1/1998 | Jyouno et al. | 204/428 |

FOREIGN PATENT DOCUMENTS

| | | | |
|---|---|---|---|
| 0 668 438 | 8/1995 | (EP) | F01N/7/00 |
| 0 822 410 | 2/1998 | (EP) | G01N/27/407 |
| 50-14396 | 2/1975 | (JP) . | |
| 53-50888 | 5/1978 | (JP) | G01N/27/58 |
| 54-89686 | 7/1979 | (JP) | G01N/27/58 |

*Primary Examiner*—Hezron Williams
*Assistant Examiner*—Jay L. Politzer
(74) *Attorney, Agent, or Firm*—Sughrue, Mion, Zinn, Macpeak & Seas, PLLC

(57) ABSTRACT

An oxygen sensor is disposed behind an exhaust gas purifying catalyst for an internal combustion engine and which suppresses the influence of unburnt hydrocarbon on the output voltage. A sensor element 1 is provided with a detection electrode 4 on the outer face of a zirconia ceramic body 2, a reference electrode 3 on the inner face of the ceramic body 2 and a spinel protective layer 5 on the outer surface of the detection electrode 4. The tip end of the sensor element 1 is covered with a protective cover 10 which is provided with an outer partition wall 11 having through holes 11$a$ and an inner partition wall 12 having through holes 12$a$. In a case where the pressure difference between the inside and outside of the protective cover 10 is $\Delta P$(atm) when the atmospheric air with a volume flow rate $Q$(L/min) is passed into the protective cover 10 from the outside, the ratio $\Delta P/Q^2$ is $3.2 \times 10^{-5}$ (atm·min$^2$·L$^{-2}$). When the surface temperature of the sensor element 1 is changed in a range of sensor active temperature, the reversing time is substantially constant. Therefore, the catalyst deterioration can be detected by the oxygen sensor with high accuracy.

13 Claims, 8 Drawing Sheets

FIG. 3 MEASURING DEVICE

WHEN CATALYST IS NORMAL

WHEN CATALYST IS DETERIORATED

WHEN UNBURNT METHANE IS BURNT

WHEN CATALYST IS NORMAL

WHEN CATALYST IS DETERIORATED

Time, sec

— — — OXYGEN SENSOR BEFORE CATALYST

——— OXYGEN SENSOR BEHIND CATALYST

OXYGEN SENSOR

FIELD OF THE INVENTION

The present invention relates to an oxygen sensor disposed behind, i.e., downstream from a catalyst in an exhaust system, particularly to an oxygen sensor for CNG (compressed natural gas) engine.

BACKGROUND OF THE INVENTION

As a measure of the purifying capability of a catalyst for purifying exhaust gas from a gasoline engine (hereinafter referred to as the catalyst), the oxygen storage capability of the catalyst has been heretofore noted. It is known that the deterioration degree of the catalyst is estimated by measuring the oxygen storage capability with an oxygen sensor. The deterioration degree is the amount by which a catalyst has deteriorated, that is, by how much it has lost its effectiveness, from use over time. Examples of a method of detecting the catalyst deterioration include the following:

First Catalyst Deterioration Detecting Method

For example, in a case where an air/fuel ratio is controlled, via a carburetor or fuel injector, or by addition/reduction of air via a catalyst air pump, based on an output of an oxygen sensor disposed downstream from the catalyst, the deterioration degree of the catalyst can be estimated based on the output of the oxygen sensor. Note that the output voltage is inversely proportional to the oxygen at the sensor.

Specifically, as shown in FIG. 7A, at a time when the voltage output of the oxygen sensor downstream from the catalyst rises, the air/fuel ratio is controlled toward a lean side. At a time when the output of the oxygen sensor falls, the air/fuel ratio is controlled toward a rich side. Here, when the purifying efficiency of the catalyst is high, even if the air/fuel ratio is controlled toward the lean side when the output of the oxygen sensor downstream from the catalyst rises, the oxygen storage capability of the catalyst is high, so that oxygen is stored. Therefore, the output voltage of the oxygen sensor downstream from the catalyst still remains high. The output voltage does not drop until oxygen is sufficiently stored. Subsequently, when the output voltage lowers, the air/fuel ratio is controlled to the rich side. Since the stored oxygen is consumed, the output voltage of the oxygen sensor downstream from the catalyst still remains low. The output voltage does not increase until the stored oxygen is consumed. As aforementioned, when the purifying efficiency of the catalyst is high, a reversing time, i.e., a high-output keeping time plus a low-output keeping time is lengthened. When the purifying efficiency of the catalyst is lowered, however, the oxygen storage capability of the catalyst is lowered. Therefore, the reversing time is shortened as shown in FIG. 7B. Therefore, the deterioration degree of the catalyst can be detected by tracing the output voltage of the oxygen sensor downstream from the catalyst and judging whether the reversing time is long or short.

Second Catalyst Deterioration Detecting Method

In a case where the air/fuel ratio is controlled based on an output of an oxygen sensor disposed upstream from the catalyst, the deterioration degree of the catalyst is estimated based on an output of an oxygen sensor disposed downstream from the catalyst.

Specifically, when the purifying efficiency of the catalyst is high, the oxygen storage capability of the catalyst is high. Therefore, the change of the air/fuel ratio toward the rich/lean side in the exhaust gas before passing through the catalyst, i.e., the change of an oxygen partial pressure, is moderated by passing the exhaust gas through the catalyst. Specifically, as shown in FIG. 8A, irrespective of whether the air/fuel ratio of the exhaust gas before passing through the catalyst is rich or lean, the oxygen partial pressure of the exhaust gas after passing through the catalyst is reduced. The amplitude of the output voltage wave form of the oxygen sensor downstream from the catalyst is reduced. However, when the purifying efficiency of the catalyst is lowered, the oxygen storage capability of the catalyst is lowered. Therefore, even after the exhaust gas is passed through the catalyst, the change of the air/fuel ratio to the rich/lean side in the exhaust gas before passing through the catalyst is kept as it is and fails to be moderated. Specifically, as shown in FIG. 8B, the change of the air/fuel ratio to the rich/lean side in the exhaust gas before passing through the catalyst results in the change in the oxygen partial pressure of the exhaust gas after passing through the catalyst. The amplitude of the output voltage wave form of the oxygen sensor downstream from the catalyst is increased in the same manner as in the front oxygen sensor. Therefore, the deterioration degree of the oxygen storage capability of the catalyst can be detected by tracing the change of the output voltage of the oxygen sensor downstream from the catalyst and judging whether the amplitude of the output voltage wave form is large or small.

However, in a case where the deterioration degree of the catalyst for an engine using compressed natural gas or CNG fuel or the like is estimated in the same manner as the first or second catalyst deterioration detecting method, defects arise and the catalyst deterioration cannot be detected.

Specifically, even when the purifying ratio of the catalyst is high, that is, when the catalyst has not deteriorated, in the first catalyst deterioration detecting method, as shown in FIG. 7C, the reversing time of the output voltage of the oxygen sensor downstream from the catalyst is shortened in a certain temperature range in the same manner as when the catalyst has deteriorated, because of the influence of a large amount of methane contained in the CNG fuel. Furthermore, in the second catalyst deterioration detecting method, as shown in FIG. 8B, the problem is that the amplitude of the output voltage wave form of the oxygen sensor downstream from the catalyst changes in the same manner as when the catalyst has deteriorated.

More specifically, since the methane contained in the exhaust gas is not sufficiently burnt even after passing through the catalyst, unburnt methane remains. When a detection electrode of the oxygen sensor downstream from the catalyst has a low temperature, however, the unburnt methane does not react with oxygen in the vicinity of the detection electrode. Therefore, no change occurs in the oxygen partial pressure, and the output voltage of the oxygen sensor downstream from the catalyst is not influenced.

However, in the first catalyst deterioration detecting method, when the temperature of the detection electrode of the oxygen sensor downstream from the catalyst reaches or exceeds a certain temperature, the unburnt methane causes a burning reaction with the oxygen on the detection electrode. Therefore, a difference in oxygen concentration between a reference electrode and the detection electrode changes in accordance with the concentration of methane. If the amount of methane exceeds the stoichiometric amount at a time when methane causes a burning reaction with the oxygen in the exhaust gas, the oxygen of the detection electrode is drawn away. Therefore, the output voltage is largely raised. If the amount of methane is equal to or less than the stoichiometric amount, no oxygen at the detection electrode is drawn away. Therefore, the output voltage is lowered. As a result, the reversing time depends on the methane concentration, but does not depend on the oxygen storage capability of the catalyst. The burning reaction becomes significant as the temperature of the detection electrode rises. Therefore, the reversing time of the oxygen sensor downstream from the catalyst becomes shorter as the temperature of the detection electrode rises.

Also, in the second catalyst deterioration detecting method, when the temperature of the detection electrode of the oxygen sensor downstream from the catalyst reaches or exceeds a certain temperature, the unburnt methane causes a burning reaction with the oxygen at the detection electrode. Since the oxygen at the detection electrode is drawn away, a difference in the oxygen partial pressure is generated. The output voltage is largely raised in accordance with the methane concentration, i.e., when the methane concentration is high or the air/fuel ratio is rich. For this reason, even if the catalyst is normal, the output voltage of the oxygen sensor downstream from the catalyst changes in accordance with the change of the air/fuel ratio toward rich/lean. Therefore, the catalyst deterioration cannot be detected.

As aforementioned, in the case where the deterioration degree of the catalyst for the engine using the CNG fuel or the like is detected based on an output signal of the oxygen sensor downstream from the catalyst, a problem remains unsolved in that the output voltage of the oxygen sensor downstream from the catalyst is not stabilized because of the burning reaction of the oxygen in the vicinity of the detection electrode with the unburnt methane.

SUMMARY OF THE INVENTION

Wherefore, an object of the present invention is to provide an oxygen sensor which is disposed downstream from a catalyst for purifying exhaust gas from an internal combustion engine and which can suppress an influence of unburnt hydrocarbon on an output voltage.

To attain this and other objects, the present invention provides an oxygen sensor which is provided with a sensor element having a detection electrode on one surface of a solid electrolyte with oxygen ion conductivity and a reference electrode on the other surface thereof; a protective cover for covering the sensor element; and a gas flow passage provided in the protective cover in such a manner that gas can flow both from the inside to the outside and from the outside to the inside of the protective cover. The oxygen sensor is disposed behind an exhaust gas purifying catalyst for an internal combustion engine using fuel containing hydrocarbon having a ratio of hydrogen to carbon of 3:1 or more (H/C$\geq$3).

The amount of the gas passing through the gas flow passage of the protective cover is restricted in such a manner that while the output voltage of the oxygen sensor varies in accordance with the concentration of hydrogen or carbon monoxide, the output voltage dependent on the concentration of the hydrocarbon does not exceed a reference level with which it is determined whether the air/fuel ratio is rich or lean.

As the solid electrolytic body having the oxygen ion conductivity, ceramics such as a ceramic mainly composed of zirconium oxide are preferable. The solid electrolytic body can be obtained by mixing raw-material powder of zirconium oxide or the like with sintering assistant powder of yttrium oxide, silicon oxide, magnesium oxide or the like, granulating the mixture, forming a predetermined configuration, calcining as the case may be, and subsequently sintering.

As aforementioned, when the solid electrolytic body is prepared, after mixing and granulating, the predetermined configuration, e.g., a cup or bottomed cylindrical configuration, a plate configuration or the like is formed. The forming is performed in a rubber pressing or by another pressing method, a thick-film or other laminating method, or the like.

The detection electrode and the reference electrode formed on the solid electrolytic body are each formed as a thin-film electrode of a conductive material mainly composed of a noble metal element having a catalyst action to promote the burning of hydrocarbon or another unburnt gas, e.g., at least one component selected from the group consisting of platinum, rhodium, palladium, ruthenium, osmium, iridium and the like. These electrodes can be formed in a plating method, a sputtering method, a pyrolysis of metal-salt, or the like.

The protective cover is usually formed on one or more partition walls. A through hole made in the partition wall forms a gas flow passage.

The oxygen sensor of the invention is suitable for detecting the deterioration of the catalyst for the internal combustion engine which uses the fuel containing hydrocarbon with the hydrogen/carbon ratio of 3:1 or more. Even after passing through a normal catalyst, the hydrocarbon with the hydrogen/carbon ratio of 3:1 or more represented by methane remains unburnt in the catalyst, and reaches the oxygen sensor disposed downstream from the catalyst as it is. When the temperature of the detection electrode of the oxygen sensor is sufficiently high, the hydrocarbon is burnt around the detection electrode. Therefore, the oxygen around the detection electrode is consumed, thereby lowering the oxygen partial pressure and raising the output voltage.

Here, even if the exhaust gas having passed through the normal catalyst contains unburnt hydrocarbon, the unburnt hydrocarbon should have no influence on the determination of the rich/lean state. In this respect, according to the oxygen sensor of the present invention, the amount of gas passing through the gas flow passage of the protective cover is restricted such that the output voltage dependent on the concentration of methane or another hydrocarbon does not exceed the reference level for determining the air/fuel ratio to be rich or lean. Therefore, even when the output voltage is raised by burning the unburnt methane around the detection electrode, the output voltage does not exceed the reference level.

The reaction is not entirely clear, but it is supposed that by restricting the amount of gas flowing through the gas flow passage of the protective cover, the concentration variation of the hydrocarbon reaching the sensor element is moderated, and the concentration variation of the hydrocarbon is retarded as compared with the reaction time of the hydrocarbon with oxygen on the detection electrode of the sensor element, so that the reversing time or the amplitude of the output voltage of the oxygen sensor is inhibited from rapidly varying due to the temperature of the oxygen sensor element.

According to the oxygen sensor of the present invention, the influence of unburnt hydrocarbon on the output voltage can be suppressed. As a result, the deterioration of the catalyst can be effectively detected with high accuracy. Specifically, the deterioration can be highly accurately detected in either the first or second conventional catalyst deterioration detecting method described above.

In the oxygen sensor of the present invention, the amount of gas flowing through the gas flow passage of the protective cover is preferably limited in such a manner that, at a predetermined temperature range of 400° C. or higher, the output voltage dependent on the concentration of the hydrocarbon does not exceed the reference level for determining the air/fuel ratio to be rich or lean. The reason is that the detection electrode may not be sufficiently activated at a temperature less than 400° C. because of the variation natural caused by long-term use. In this case, the reversing time does not vary because of deterioration, or the amplitude becomes substantially constant, so that the deterioration of the catalyst cannot be detected.

Moreover, in the oxygen sensor of the present invention, the reference level is preferably determined in a range of 400 to 600 mV. If the reference level is outside the range, the center of the amplitude of the output voltage wave form of the oxygen sensor has deviated. Since the reversing time becomes irregular, it is difficult to detect the catalyst deterioration with a sufficient accuracy.

Furthermore, in the oxygen sensor of the present invention, assuming that a pressure difference between the inside and the outside of the protective cover is $\Delta P(atm)$, when the atmospheric air having a volume flow rate $Q(L/min)$ is passed through the protective cover from the outside, the ratio $\Delta P/Q^2$ of the pressure difference ($\Delta P$) and the squared volume flow rate ($Q^2$) meet the condition represented in the following expression (1). In this case, the range from 400° C. or higher, where the output voltage dependent on the concentration of the hydrocarbon does not exceed the reference level for determining the air/fuel ratio to be rich or lean, i.e., the range where the concentration change of the hydrocarbon does not influence the reversing time or amplitude is preferably broadened for practical use.

$$\Delta P/Q^2 > 1 \times 10^{-5} (atm \cdot min^2 \cdot L^{-2}) \quad (1)$$

Especially, the condition represented in the following expression (2) is preferably satisfied. In this case, the aforementioned range is broadened substantially all over the active temperature range of the sensor element.

$$\Delta P/Q^2 > 2 \times 10^{-5} (atm \cdot min^2 \cdot L^{-2}) \quad (2)$$

Moreover, the condition represented in the following expression (3) is preferably satisfied. If $\Delta P/Q^2$ exceeds $1 \times 10^{-3}$, the sensor response tends to be significantly retarded, and requires a longer time for determining the catalyst deterioration.

$$\Delta P/Q^2 < 1 \times 10^{-3} (atm \cdot min^2 \cdot L^{-2}) \quad (3)$$

Furthermore, in the oxygen sensor of the present invention, the protective cover is formed by one or more partition walls. For the partition wall having a minimum total opening area, the condition represented in the following expression (4) is preferably satisfied. If the total opening area (A) exceeds the range, the variation of methane exerts an influence on the reversing time or the amplitude of the output voltage of the oxygen sensor. If the total opening area (A) is less than the range, the sensor response tends to be significantly retarded, and requires a longer time for determining the catalyst deterioration.

$$0.1 < A < 10 (mm^2) \quad (4)$$

DETAILED DESCRIPTION OF PREFERRED EMBODIMENT

FIRST EXAMPLE

After blending $Y_2O_3$ having a purity of 99% or more with $ZrO_2$ having a purity of 99% or more in the proportion of 5 mol to 100 mol and wet-mixing the mixture, calcining was performed at 1300° C. Water was applied to the calcined material. Subsequently, after grinding in a ball mill, water-soluble binder was applied, and granulation was performed via a spray-drying method.

The granulated material was formed into a cup or bottomed cylindrical configuration using a rubber pressing method, and ground with a grindstone. Subsequently, by sintering the formed material at 1500° C. for three hours, a zirconia ceramic body was obtained. A platinum thin film having a thickness of 1 to 2 $\mu$m was formed on the exterior periphery of the ceramic body in an electroless plating method to form a detection electrode. Thereafter, the platinum thin film was thermally treated in an atmospheric environment at 1200° C. for 90 minutes. Thereby, the denseness of the platinum thin film constituting the detection electrode was enhanced and stabilized.

Figure 1:
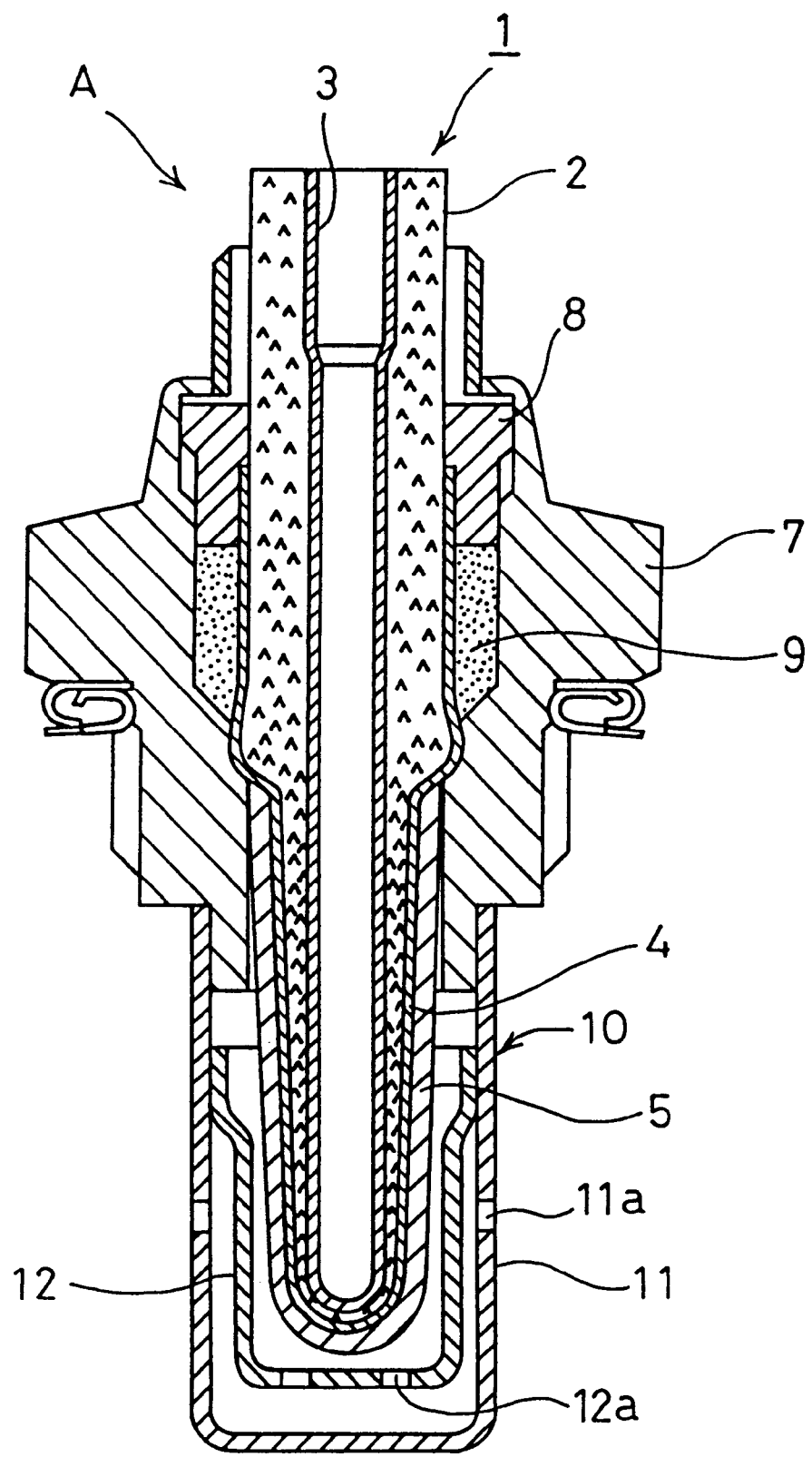
FIG. 1 is a cross-sectional view of an oxygen sensor according to the present invention.

Subsequently, a platinum thin film with a thickness of 1 to 2 $\mu$m was deposited on the inner face of the ceramic body by electroless plating to obtain a reference electrode. Moreover, so as to protect the detection electrode, an about 200 $\mu$m thick protective layer of spinel powder of magnesium aluminate was formed on the outer surface of the detection electrode by plasma spay coating. The ceramic body was exposed to combustion gas, and subjected to the aging process to form a sensor element 1 shown in FIG. 1. In the sensor element 1, a detection electrode 4 is on the outer face of a zirconia ceramic body 2 as the solid electrolyte having oxygen ion conductivity, a reference electrode 3 is on the inner face of the ceramic body 2, and a spinel protective layer 5 is on the outer surface of the detection electrode 4.

Figure 2:
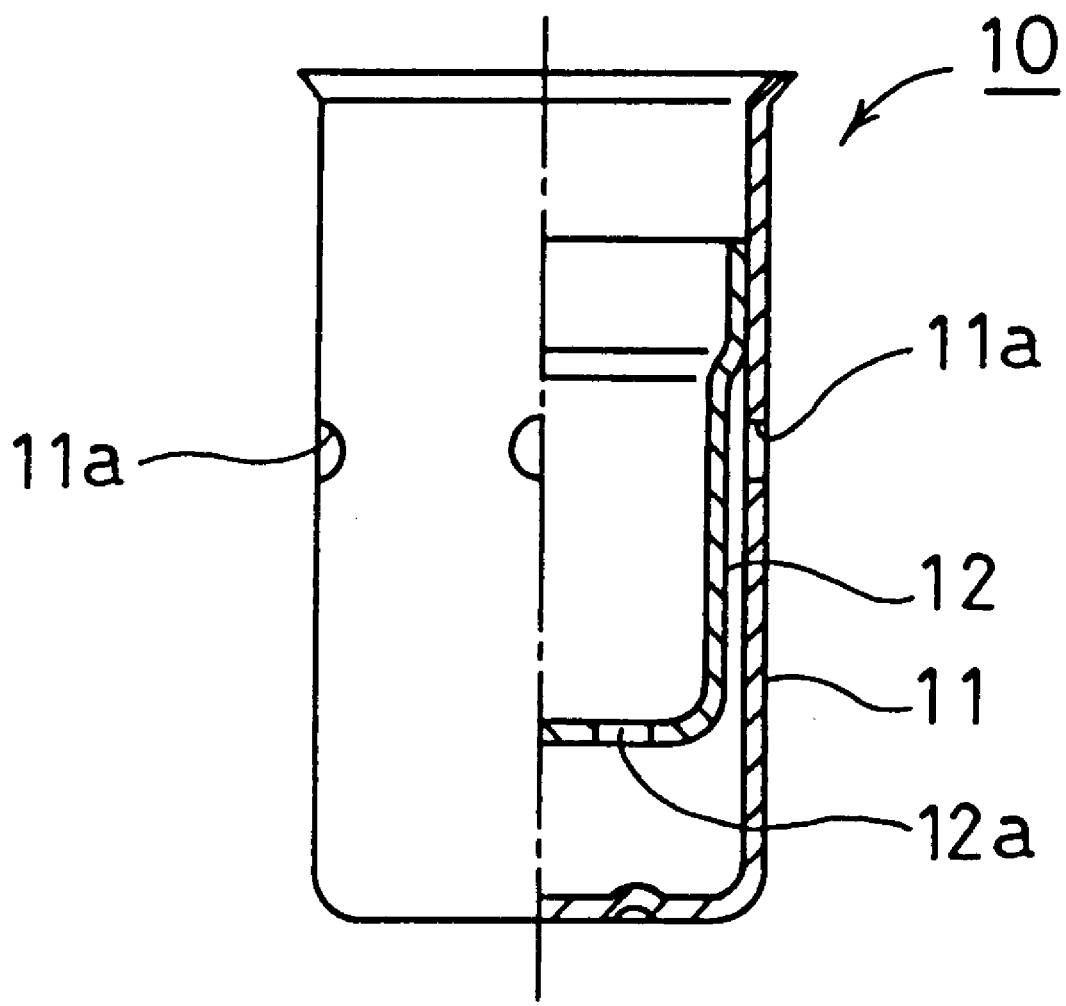
FIG. 2 is a partial cross-sectional view of a protective cover according to the first embodiment of the present invention.

Subsequently, after the sensor element 1 was set in a metal case 7, a caulking ring 8 and a talc or another filler 9 were inserted to fix the sensor element 1 in the metal case 7. A protective cover 10 was prepared, as shown in FIG. 2, by welding the periphery of an enlarged opening edge of an inner partition wall 12 having a plurality of through holes 12a to an outer partition wall 11 having a plurality of through holes 11a. The opening edge of the protective cover 10 was welded to the metal case 7 while the tip end of the sensor element 1 was covered with the protective cover 10. Subsequently, lead wires (not shown) were connected to the detection electrode 4 and the reference electrode 3, and the sensor element 1 was covered with an outer cylindrical member (not shown), so that the oxygen sensor for the CNG engine was completed. In the embodiment, the through holes 11a and 12a form a gas flow passage of the present invention. Additionally, the total opening area defined by the through holes 12a of the inner partition wall 12 was set to 1.1 mm$^2$, while the total opening area defined by the through holes 11a of the outer partition wall 11 was set to 3.1 mm$^2$.

Figure 3:
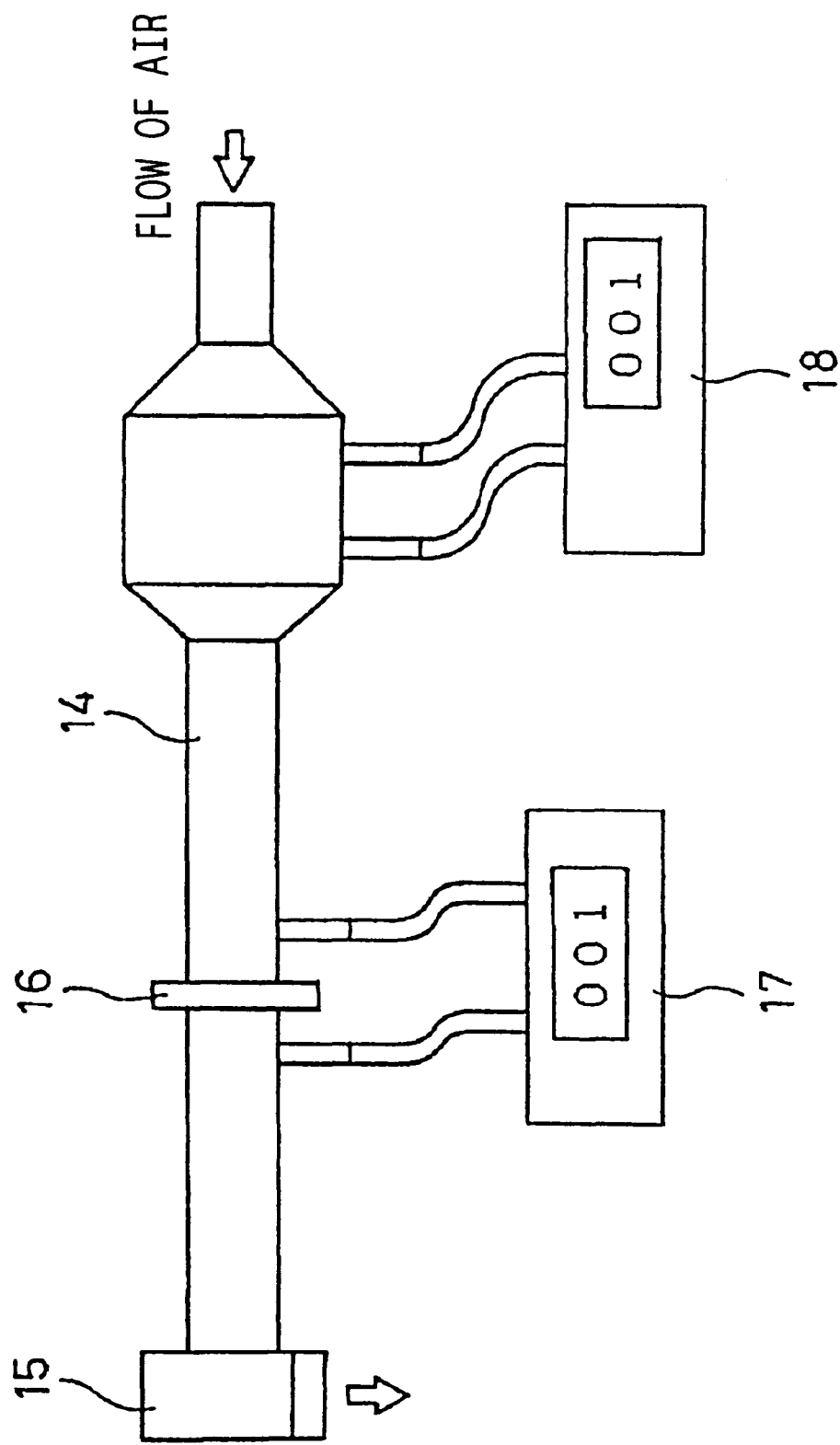
FIG. 3 is a diagrammatic view showing a measuring device for measuring the volume flow rate $Q(L/min)$ through the protective cover and the pressure difference $\Delta P(atm)$ between the inside and the outside of the protective cover.
Figure 4:
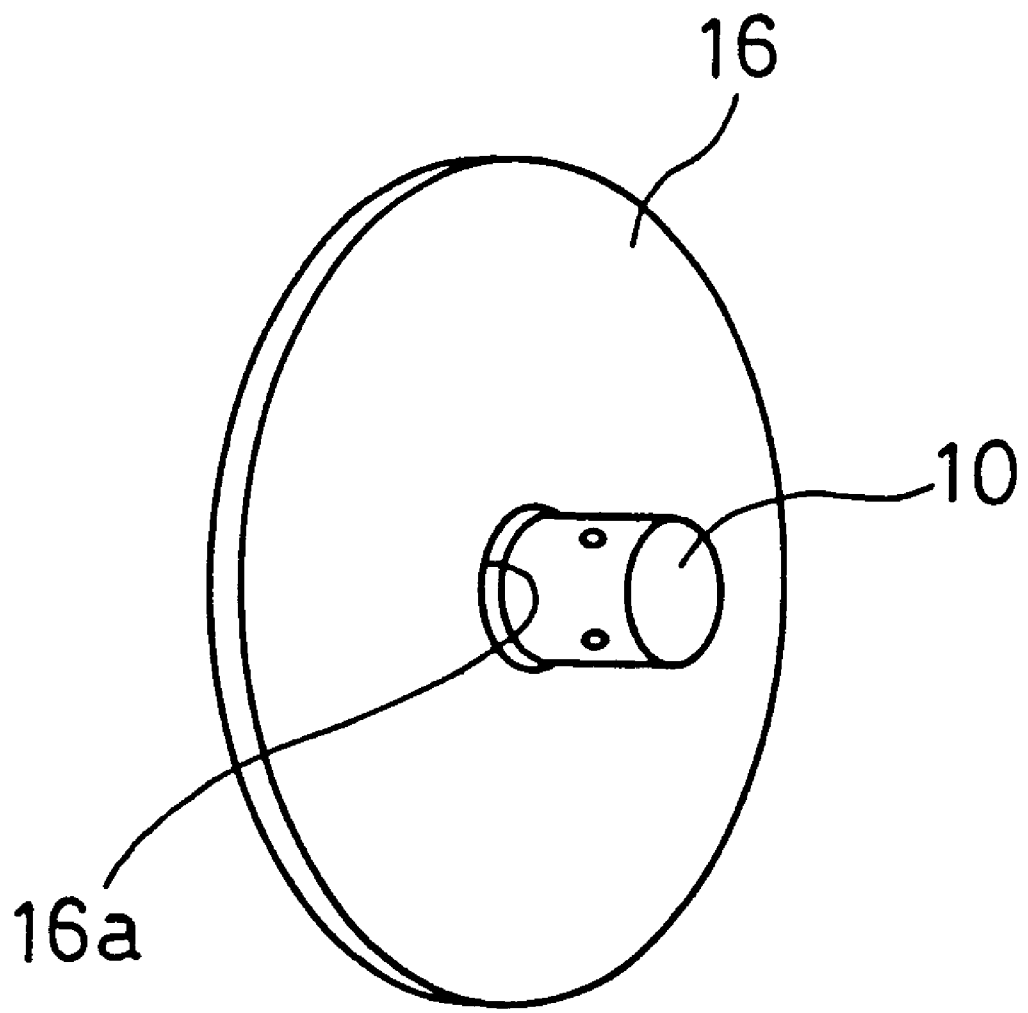
FIG. 4 is a perspective view of a partition plate for use in the measuring device shown in FIG. 3.

The volume flow rate Q(L/min) and the pressure difference ΔP(atm) between the inside and outside of the protective cover 10 at the time of passing the atmospheric air through the protective cover 10 were measured by a measuring device shown in FIG. 3. As shown in FIG. 3, in the measuring device, a fan 15 is attached to one end of a pipe 14 simulating an exhaust pipe, and a partition plate 16 is attached to the substantial center of the pipe 14. A differential pressure gauge 17 is attached to the pipe 14 for measuring a differential pressure between upstream and downstream from the partition wall 16, while a laminar flow rate meter 18 is attached to the pipe 14 for measuring the volume flow rate of the air flowing into the pipe 14. As shown in FIG. 4, an attachment hole 16a for mounting the protective cover 10 is made in the substantial center of the partition wall 16. The protective cover 10 is inserted and fixed into the attachment hole 16a by welding or otherwise. In operation, the fan 15 of the measuring device is rotated to generate the flow of air in the pipe 14 in the direction shown by an arrow in FIG. 3. Then, the value ΔP(atm) on the differential pressure gauge 17 and the value Q(L/min) of the laminar flow rate meter 18 are read to obtain the ratio $\Delta P/Q^2$. In the example, the ratio was $3.2 \times 10^{-5}$ (atm·min$^2$·L$^{-2}$).

Figure 5:
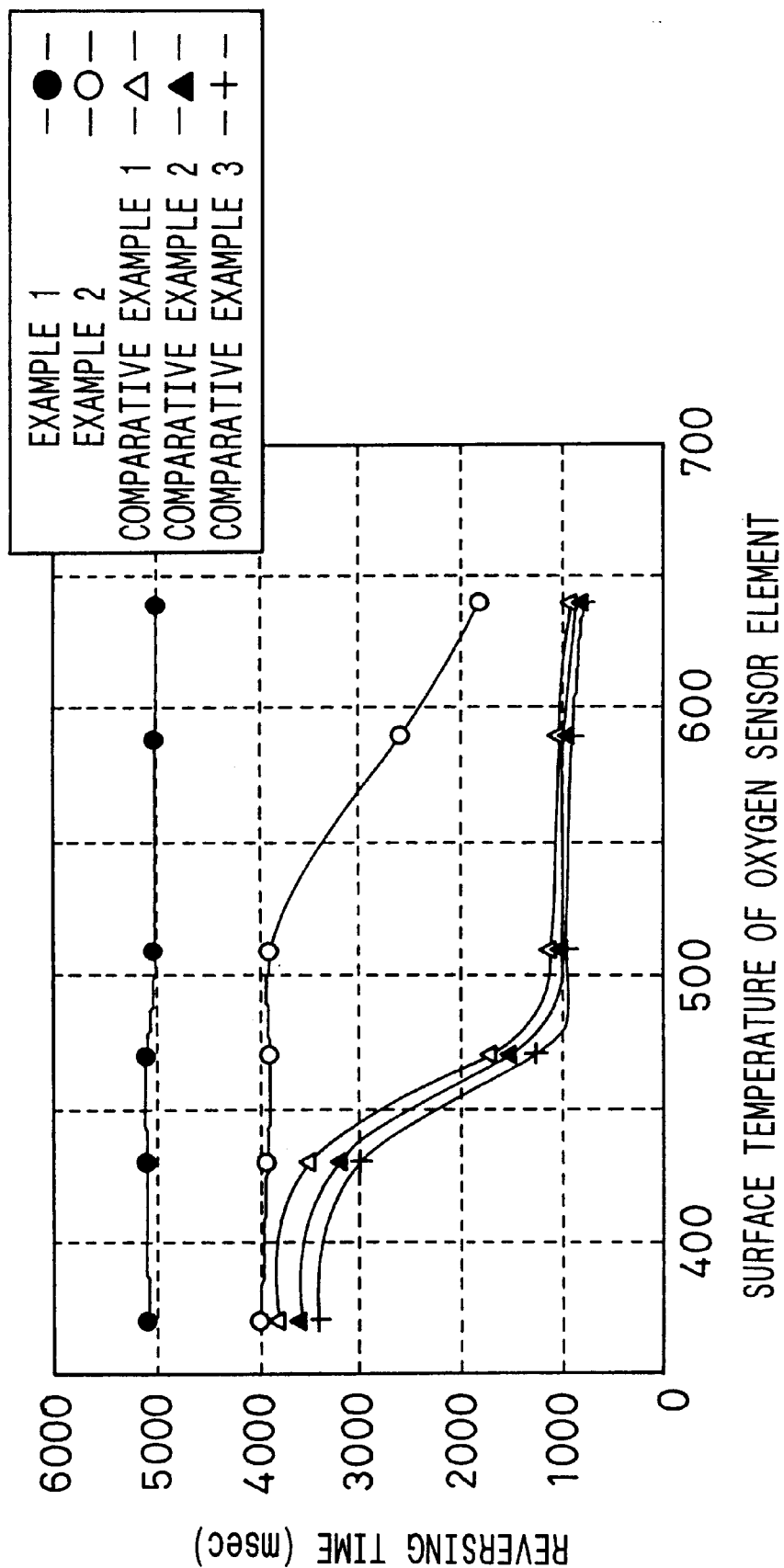
FIG. 5 is a graph showing the relationship of the element surface temperature of the oxygen sensor and the reversing time.

The oxygen sensor of the first example was mounted behind a new exhaust gas purifying catalyst. It was judged by the first conventional catalyst deterioration detecting method whether or not the catalyst deterioration can be determined by the output of the oxygen sensor. As a result, in the oxygen sensor of the first example, as shown in FIG. 5, when the surface temperature of the sensor element 1 was varied in the sensor active temperature range of 350 to 650° C., the reversing time, i.e., the high output retention time plus the low output retention time was substantially constant. Specifically, in the oxygen sensor of the first example, the amount of gas passing through the through holes 11a and 12a of the protective cover 10 is restricted in such a manner that the output voltage dependent on the methane contained in CNG gas does not exceed the reference level for determining the air/fuel ratio to be rich or lean in the aforementioned temperature range. Therefore, even if the unburnt methane is burnt around the detection electrode 4, the output voltage of the oxygen sensor does not exceed the reference level. Therefore, the influence of the unburnt methane on the output voltage can be suppressed, and the catalyst deterioration can be detected with a high degree of accuracy.

SECOND EXAMPLE, FIRST TO THIRD COMPARATIVE EXAMPLES

The oxygen sensors of the examples were performed in the same manner, except that the dimensions of the through holes 11a and 12a of the protective cover 10 of the oxygen sensor of the first example were varied to provide the values of differential pressure ΔP, volume flow rate Q and total opening area A shown in Table 1. Moreover, in the same manner as the first example, it was judged by the first conventional catalyst deterioration detecting method whether or not the catalyst deterioration can be determined by the output of these oxygen sensors. Results are shown in Table 1 and FIG. 5.

TABLE 1

| | FIRST EXAMPLE | SECOND EXAMPLE | FIRST COMPARATIVE EXAMPLE | SECOND COMPARATIVE EXAMPLE | THIRD COMPARATIVE EXAMPLE |
|---|---|---|---|---|---|
| ΔP/Q$^2$ (atm · min$^2$ · L$^{-2}$) | $3.2 \times 10^{-5}$ | $1.7 \times 10^{-5}$ | $8.5 \times 10^{-6}$ | $1.2 \times 10^{-6}$ | $7.0 \times 10^{-7}$ |
| TOTAL OPENING AREA OF OUTER PARTITION WALL (mm$^2$) | 3.1 | 16.8 | 31.0 | 85.2 | 100.5 |
| TOTAL OPENING AREA OF INNER PARTITION WALL (mm$^2$) | 1.1 | 9.0 | 15.3 | 63.2 | NO INNER PARTITION WALL |
| A (mm$^2$) | 1.1 | 9.0 | 15.3 | 63.2 | 100.5 |
| CATALYST DETERIORATION JUDGMENT | ⊚ | ○ | X | X | X |

In Table 1, symbol ⊚ indicates that the catalyst deterioration can be detected and there is no dependency of the reversing time on the temperature of the sensor element, ○ indicates that the catalyst deterioration can be detected but the reversing time depends on the temperature of the sensor element, and X indicates that the catalyst deterioration cannot be detected.

Figure 6:
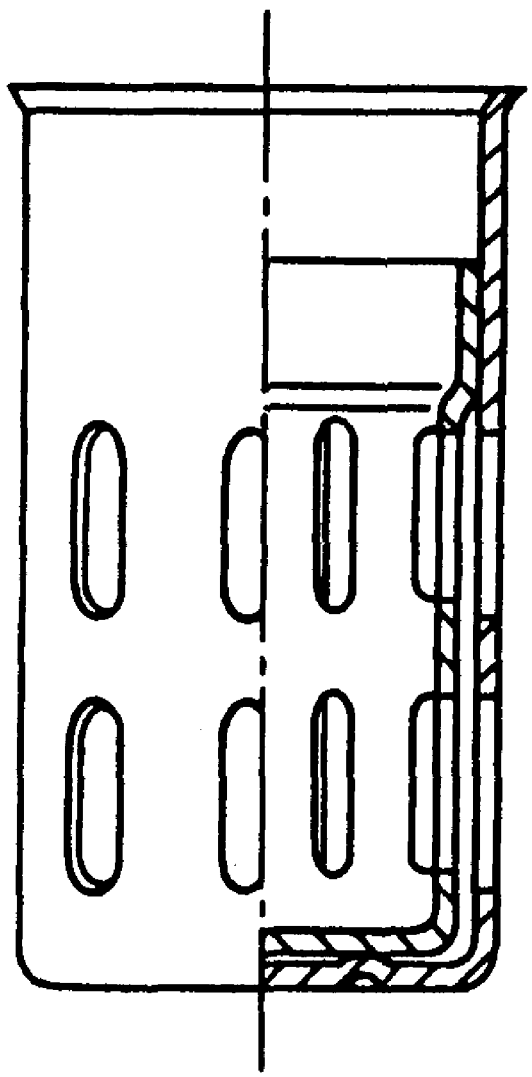
FIG. 6 is a partial cross-sectional view of a conventional protective cover.
Figure 7A:
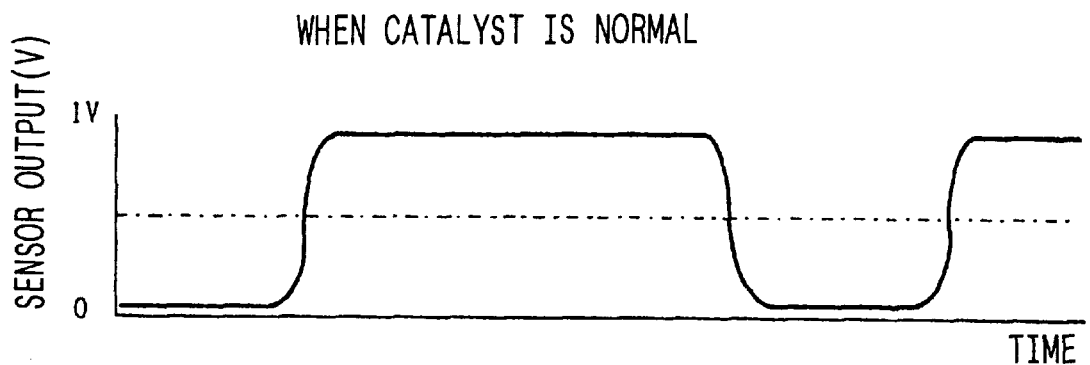
FIGS. 7A, 7B and 7C are explanatory views of the first catalyst deterioration detecting method by the oxygen sensor disposed behind a catalyst.
Figure 7B:
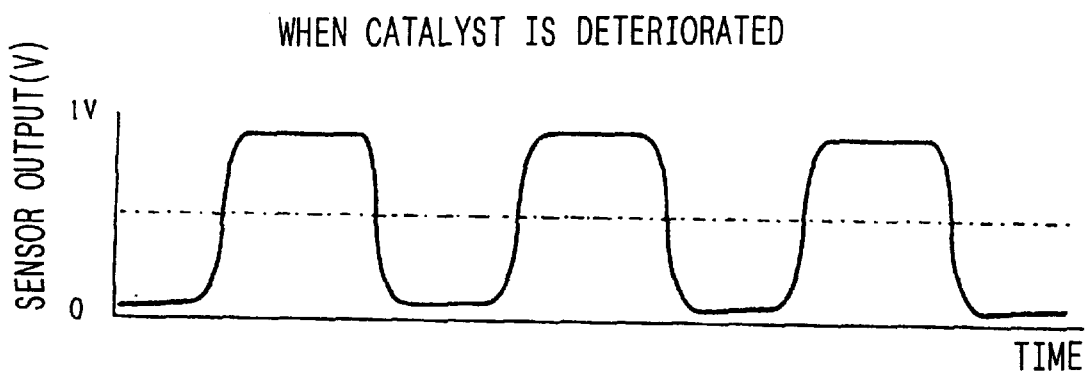
Figure 7C:
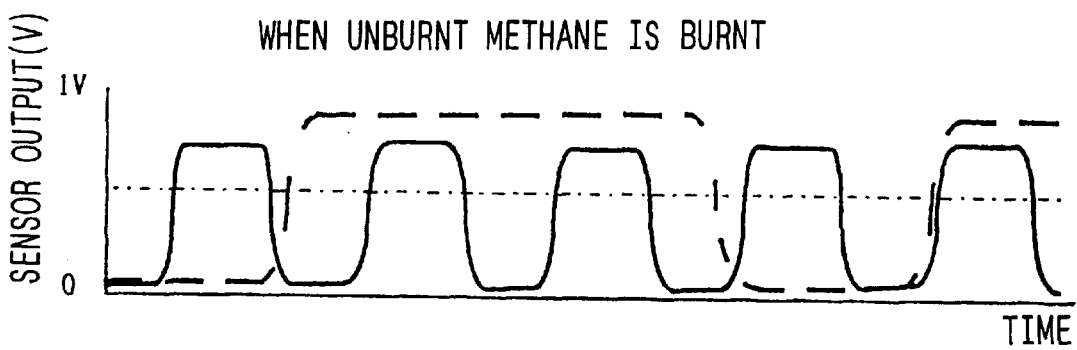
Figure 8A:
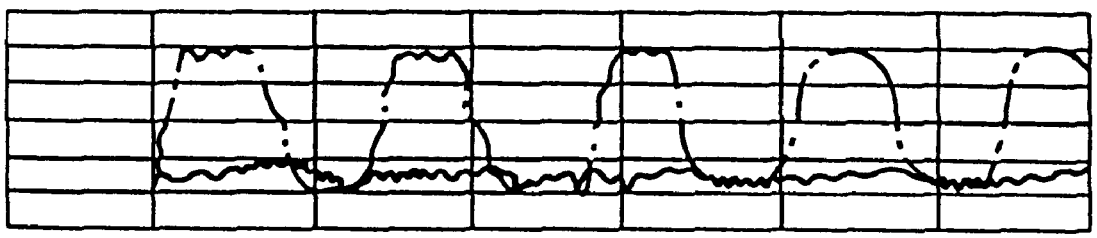
FIGS. 8A and 8B are explanatory views of the second catalyst deterioration detecting method by the oxygen sensor behind the catalyst.
Figure 8B:
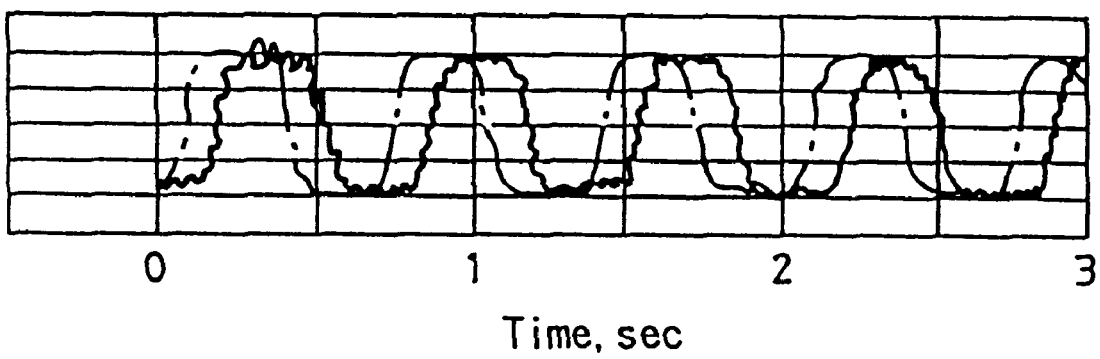

As seen from FIG. 5, in the second example, there is a region where the reversing time does not depend on the temperature of the sensor element. Therefore, by controlling the temperature in the region, the catalyst deterioration can be judged. On the other hand, in the first to third comparative examples, although the new catalyst is used, the reversing time depends on the temperature in all the active temperature range of the sensor element. Since the reversing time is shortened, it is judged that the catalyst deterioration cannot be detected. Additionally, in the third comparative example, the conventional protective cover shown in FIG. 6 is used.

Moreover, when the through holes 11a and 12a of the protective cover 10 were made smaller than in the first example and the gas flow rate was restricted in such a manner that the ratio ΔP/Q2 exceeded $1 \times 10^{-3}$ (atm·min$^2$·L$^{-2}$), the responsiveness of the oxygen sensor was remarkably retarded. Accordingly, it was judged that the element could not be used as the oxygen sensor.

The present invention is not limited to the above embodiments, and can be embodied variously within the technical scope of the attached claims.

What is claimed is:

1. An oxygen sensor disposed downstream of a catalyst, the catalyst purifying an exhaust gas from an internal combustion engine using fuel which contains hydrocarbon having a ratio of hydrogen to carbon of at lease 3:1, the oxygen sensor comprising:

a sensor element having a detection electrode on a first surface of a solid electrolyte having oxygen ion conductivity and a reference electrode on a second surface thereof, and a protective cover separating an inside cavity portion and an outside region, the cavity portion for receiving said sensor element;

a gas flow passage provided in said protective cover in such a manner that gas can flow both from the inside cavity portion to the outside, and from the outside to the inside cavity portion of said protective cover; and wherein the amount of the gas passing through the gas flow passage of said protective cover is restricted in such a manner that although an output voltage of the oxygen sensor varies in accordance with the concentration of at least hydrogen and carbon monoxide, the output voltage dependent on the concentration of said hydrocarbon does not exceed a reference level by which it is determined whether the air/fuel ratio is rich or lean.

2. The oxygen sensor according to claim 1, wherein the amount of gas flowing through the gas flow passage of said protective cover is restricted in such a manner that, in a predetermined temperature range from 400° C. or higher, the output voltage dependent on the concentration of said hydrocarbon does not exceed the reference level for determining the air/fuel ratio to be rich or lean.

3. The oxygen sensor according to claim 1, wherein said reference level is set in a range of 400 to 600 mV.

4. The oxygen sensor according to claim 1, wherein in a case where a pressure difference between the inside and outside of said protective cover is $\Delta P(atm)$ when the exhaust gas having a volume flow rate $Q(L/min)$ is passed into said sensor cavity of said protective cover from the outside, a condition represented in the following expression is satisfied:

$$\Delta P/Q^2 > 1 \times 10^{-5} (atm \cdot min^2 \cdot L^{-2}).$$

5. The oxygen sensor according to claim 4, wherein a condition represented in the following expression (2) is satisfied:

$$\Delta P/Q^2 > 1 \times 10^{-3} (atm \cdot min^2 \cdot L^{-2}).$$

6. The oxygen sensor according to claim 1 wherein said protective cover is formed by one or more partition walls, and a condition represented in the following expression is satisfied $$0.1 < A < 10 (mm^2)$$

where A is the total opening area of the gas flow passage through the partition wall having a minimum opening area.

7. An oxygen sensor located downstream of an exhaust gas purifying catalyst in an exhaust pathway of an internal combustion engine using fuel which contains hydrocarbon having a ratio of hydrogen to carbon of at least 3:1, the oxygen sensor comprising:

a sensor element having a detection electrode on a first surface of a solid electrolyte with oxygen ion conductivity and a reference electrode on a second surface thereof;

a protective cover defining a sensor cavity for receiving said sensor element, the protective cover having an inner partition wall nested within an outer partition wall defining an intermediate space therebetween;

a gas flow passage provided in said protective cover in such a manner that gas can flow both from outside said protective cover to the sensor cavity and from the cavity to the outside of said protective cover;

the gas flow passage comprising at least a first orifice in said outer partition wall and at least a second orifice in said inner partition wall, the first and second orifices communicating via said intermediate space;

wherein the gas flow passage of said protective cover restricts the flow of exhaust gas in such a manner that although an output voltage of the oxygen sensor varies in accordance with the concentration of at least hydrogen and carbon monoxide, the output voltage dependent on the concentration of said hydrocarbon does not exceed a reference level with which it is determined whether the air/fuel ratio is rich or lean.

8. The oxygen sensor as set forth in claim 7, wherein a total area defined by the at least second orifice of the inner partition wall is approximately 1.1 $mm^2$ and a total area defined by the at least first orifice of the outer partition wall is approximately 3.1 $mm^2$.

9. The oxygen sensor according to claim 7, wherein the amount of gas flowing through the gas flow passage of said protective cover is restricted in such a manner that, in a predetermined temperature range from 400° C. or higher, the output voltage dependent on the concentration of said hydrocarbon does not exceed the reference level for determining the air/fuel ratio to be rich or lean.

10. The oxygen sensor according to claim 7, wherein said reference level is set in a range of 400 to 600 mV.

11. The oxygen sensor according to claim 7, wherein a pressure difference between the outside of said protective cover and the sensor cavity is defined as $\Delta P(atm)$ where the exhaust gas has a volumetric flow rate $Q(L/min)$ in the exhaust pathway, a condition represented in the following expression is satisfied:

$$\Delta P/Q^2 > 1 \times 10^{-5} (atm \cdot min^2 \cdot L^{-2}).$$

12. The oxygen sensor according to claim 11, wherein the condition as represented in the following expression (2) is satisfied:

$$\Delta P/Q^2 > 1 \times 10^{-3} (atm \cdot min^2 \cdot L^{-2}).$$

13. The oxygen sensor according to claim 7, wherein a condition represented in the following expression is satisfied:

$$0.1 < A < 10 (mm^2)$$

where A is the total opening area of the at least second orifice of the inner partition wall.

* * * * *

UNITED STATES PATENT AND TRADEMARK OFFICE
CERTIFICATE OF CORRECTION

PATENT NO. : 6,182,498 B1
DATED : February 6, 2001
INVENTOR(S) : Akio Mizutani, Teppei Okawa, Hiroshi Kubota, Seiichi Hosogai and Hiroyuki Fujita It is certified that error appears in the above-identified patent and that said Letters Patent is hereby corrected as shown below:

Title page,
Item [73], Assignee: delete "NGK Spark Plug Co., Ltd." please insert -- NGK Spark Plug Co., Ltd. and Honda Motor Co., Ltd. --

Signed and Sealed this

Thirtieth Day of April, 2002

Attest:

Attesting Officer

JAMES E. ROGAN
*Director of the United States Patent and Trademark Office*